US011819214B2

(12) United States Patent
Lorenzo et al.

(10) Patent No.: US 11,819,214 B2
(45) Date of Patent: Nov. 21, 2023

(54) HELICAL BALLOON ASSIST DEVICE AND METHOD FOR USING THE SAME

(71) Applicant: DePuy Synthes Products, Inc., Raynham, MA (US)

(72) Inventors: Juan Lorenzo, Davie, FL (US); Kirk Johnson, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 497 days.

(21) Appl. No.: 17/148,867

(22) Filed: Jan. 14, 2021

(65) Prior Publication Data
US 2021/0128164 A1 May 6, 2021

Related U.S. Application Data

(62) Division of application No. 15/941,166, filed on Mar. 30, 2018, now Pat. No. 10,918,390.

(51) Int. Cl.
*A61B 17/12* (2006.01)
*A61M 25/06* (2006.01)
(Continued)

(52) U.S. Cl.
CPC .... *A61B 17/12136* (2013.01); *A61B 17/1204* (2013.01); *A61B 17/12036* (2013.01);
(Continued)

(58) Field of Classification Search
CPC .............. A61B 1/00131–0014; A61B 17/12022–12136; A61B 17/22032;
(Continued)

(56) References Cited

U.S. PATENT DOCUMENTS 3,811,448 A * 5/1974 Morton ............. A61M 25/0017
604/102.02
4,762,130 A * 8/1988 Fogarty ............. A61M 25/0125
604/908
(Continued)

FOREIGN PATENT DOCUMENTS

CN 101919737 A 12/2010
CN 104619375 A 5/2015
(Continued)

OTHER PUBLICATIONS

Extended European Search Report for European Application No. 19166296.4, dated Aug. 29, 2019, 7 Pages.
(Continued)

*Primary Examiner* — Tan-Uyen T Ho
*Assistant Examiner* — Charles M Wei
(74) *Attorney, Agent, or Firm* — TROUTMAN PEPPER HAMILTON SANDERS LLP

(57) ABSTRACT

The helical balloon assist device includes a tubular balloon formed at least partially into an independent helical shape in an uninflated state and an inflation tube in sealed communication with the balloon and extending from the helical balloon assist device in a proximal direction. The helical balloon assist device may include an inner core member formed at least partially into an independent helical shape and supporting the helical shape of the tubular balloon.

20 Claims, 6 Drawing Sheets

(51) Int. Cl.
*A61M 25/10* (2013.01)
*A61B 17/00* (2006.01)

(52) U.S. Cl.
CPC ... *A61B 17/12109* (2013.01); *A61M 25/0662* (2013.01); *A61M 25/1002* (2013.01); *A61B 2017/00862* (2013.01); *A61B 2017/1205* (2013.01); *A61M 2025/0681* (2013.01)

(58) Field of Classification Search
CPC .............................. A61B 2017/22051; A61B 2017/22065–22071; A61B 2018/00285; A61M 25/0662; A61M 25/10–2025/1097
See application file for complete search history.

(56) References Cited

U.S. PATENT DOCUMENTS

| | | | |
|---|---|---|---|
| 5,181,911 A * | 1/1993 | Shturman | A61M 25/104 604/103.07 |
| 5,211,654 A | 5/1993 | Kaltenbach | |
| 5,226,888 A * | 7/1993 | Arney | A61M 25/1002 604/509 |
| 5,295,958 A * | 3/1994 | Shturman | A61M 60/896 606/159 |
| 5,549,555 A | 8/1996 | Sohn | |
| 5,554,119 A * | 9/1996 | Harrison | A61M 25/1002 604/101.05 |
| 5,772,681 A * | 6/1998 | Leoni | A61M 25/104 606/198 |
| 5,797,948 A * | 8/1998 | Dunham | A61M 25/10 604/101.02 |
| 5,843,027 A | 12/1998 | Stone et al. | |
| 5,855,546 A * | 1/1999 | Hastings | A61N 5/1002 600/3 |
| 5,882,334 A | 3/1999 | Sepetka et al. | |
| 5,919,163 A | 7/1999 | Glickman | |
| 6,196,996 B1 * | 3/2001 | Teirstein | A61M 25/1002 604/508 |
| 6,391,037 B1 | 5/2002 | Greenhalgh | |
| 6,398,708 B1 | 6/2002 | Hastings et al. | |
| 6,409,652 B1 * | 6/2002 | Kamdar | A61N 5/1002 600/3 |
| 6,544,276 B1 | 4/2003 | Azizi | |
| 6,575,932 B1 | 6/2003 | O'Brien et al. | |
| 6,666,828 B2 | 12/2003 | Greco et al. | |
| 7,081,115 B2 * | 7/2006 | Taimisto | A61B 18/1492 606/41 |
| 7,214,198 B2 | 5/2007 | Greco et al. | |
| 7,300,415 B2 | 11/2007 | McMurtry et al. | |
| 7,766,871 B2 * | 8/2010 | Hirszowicz | A61M 25/1011 604/103.07 |
| 8,079,978 B2 | 12/2011 | Hirszowicz et al. | |
| 9,149,288 B2 * | 10/2015 | Teague | A61B 17/22032 |
| 9,180,033 B2 | 11/2015 | Motaganahalli | |
| 9,232,992 B2 | 1/2016 | Heidner | |
| 9,345,864 B2 | 5/2016 | Suehara | |
| 9,398,965 B2 | 7/2016 | Motaganahalli | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 10,219,678 B2 | 3/2019 | Wake | |
| 10,286,184 B2 * | 5/2019 | Laduca | A61M 25/0155 |
| 2002/0045925 A1 * | 4/2002 | Keller | A61M 25/00 607/113 |
| 2004/0176790 A1 | 9/2004 | Coyle | |
| 2005/0070887 A1 * | 3/2005 | Taimisto | A61B 18/1492 606/41 |
| 2005/0197667 A1 * | 9/2005 | Chan | A61M 25/1025 604/97.01 |
| 2006/0030924 A1 | 2/2006 | Van Der Leest et al. | |
| 2006/0064151 A1 | 3/2006 | Guterman | |
| 2006/0074437 A1 | 4/2006 | Teague et al. | |
| 2006/0287666 A1 * | 12/2006 | Saadat | A61M 25/1011 606/198 |
| 2007/0185444 A1 | 8/2007 | Euteneuer et al. | |
| 2008/0281350 A1 | 11/2008 | Sepetka | |
| 2009/0204068 A1 * | 8/2009 | Nguyen | A61M 25/008 604/101.01 |
| 2009/0209969 A1 * | 8/2009 | Wolfe | A61B 17/3439 606/108 |
| 2010/0145265 A1 * | 6/2010 | Min | A61M 25/0082 604/95.03 |
| 2010/0324649 A1 | 12/2010 | Mattsson | |
| 2011/0137331 A1 | 6/2011 | Walsh et al. | |
| 2011/0144742 A1 * | 6/2011 | Madrid | A61F 2/2433 623/2.11 |
| 2012/0029509 A1 * | 2/2012 | Smith | A61B 18/1492 606/41 |
| 2012/0226303 A1 * | 9/2012 | Roche | A61M 25/1002 606/194 |
| 2012/0245520 A1 * | 9/2012 | Kelly | A61M 25/1029 604/103.09 |
| 2012/0283768 A1 | 11/2012 | Cox et al. | |
| 2014/0067029 A1 * | 3/2014 | Schauer | A61B 18/1492 607/116 |
| 2014/0135812 A1 | 5/2014 | Divino et al. | |
| 2014/0135891 A1 * | 5/2014 | Poehlmann | A61M 25/1002 623/1.11 |
| 2014/0200607 A1 | 7/2014 | Sepetka et al. | |
| 2014/0249506 A1 * | 9/2014 | Laduca | A61F 2/958 604/509 |
| 2014/0343409 A1 | 11/2014 | Purtell et al. | |

(56) References Cited

U.S. PATENT DOCUMENTS

| | | | |
|---|---|---|---|
| 2015/0238729 A1* | 8/2015 | Jenson | A61M 25/04 604/510 |
| 2015/0320982 A1 | 11/2015 | Massicotte | |
| 2016/0095619 A1* | 4/2016 | McMahon | A61B 17/3207 606/159 |
| 2016/0310759 A1 | 10/2016 | D'Andrea | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo et al. | |
| 2017/0106173 A1 | 4/2017 | Chanduszko | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |
| 2018/0014829 A1* | 1/2018 | Tal | A61B 17/12177 |
| 2018/0263688 A1* | 9/2018 | Barrish | A61B 5/6853 |
| 2019/0298383 A1* | 10/2019 | Lorenzo | A61B 17/1204 |
| 2021/0138211 A1* | 5/2021 | Laby | A61B 1/0052 |

FOREIGN PATENT DOCUMENTS

| | | |
|---|---|---|
| CN | 105682610 A | 6/2016 |
| CN | 205434660 U | 8/2016 |
| CN | 107468295 A | 12/2017 |
| CN | 107530533 A | 1/2018 |
| EP | 0 275 230 A2 | 7/1988 |
| EP | 2589344 A1 | 5/2013 |
| JP | 63-192457 A | 8/1988 |
| JP | 2001-9045 A | 1/2001 |
| JP | 2004-529741 A | 9/2004 |
| JP | 2013-223663 A | 10/2013 |
| JP | 2014-508574 A | 4/2014 |
| JP | 2015192727 A | 11/2015 |
| JP | 2016-501679 A | 1/2016 |
| WO | WO 99/27989 A1 | 6/1999 |
| WO | WO 02/102451 A1 | 12/2002 |
| WO | WO 2015/061801 A2 | 4/2015 |
| WO | 2017/081561 A1 | 5/2017 |

OTHER PUBLICATIONS

Extended European Search Report for European Application No. 19166317.8, dated Sep. 2, 2019, 7 Pages.

Notification of Reasons for Refusal issued in Japanese Patent Application No. 2019-066459 dated Mar. 14, 2023, English translation only.

Search Report issued in Chinese Patent Application No. 201910251269.X dated Mar. 10, 2022, English translation only.

Text of Second Office Action and Search Report issued in Chinese Patent Application No. 201910251269.X dated Aug. 23, 2022, English translation only.

European Search Report issued in corresponding European Patent Application No. 19 16 6286 dated Aug. 27, 2019.

\* cited by examiner

# HELICAL BALLOON ASSIST DEVICE AND METHOD FOR USING THE SAME

CROSS-REFERENCE TO RELATED APPLICATION

This application is a divisional application of U.S. patent application Ser. No. 15/941,166, filed on Mar. 30, 2018, the disclosure of which is herein incorporated by reference in its entirety as if set forth in full.

FIELD OF INVENTION

This disclosure relates generally to the field of tools for vascular surgery. More particularly, it relates to balloon devices for occluding blood vessels during vascular surgery.

BACKGROUND

Balloon Guide Catheters facilitate the insertion of intravascular devices as well as control/restrict flow in ischemic applications. They are designed to have a large lumen to maximize clot capture, and are indicated for use as a conduit for clot retrieval devices. Because the balloon is an integral part of the assembly on these devices, the profile of the devices is very large, for example 8F (2.7 mm) (French "F"=0.33 mm) as compared to a regular large ID guide catheter which might be sized 6F (2.0 mm). Also, the overall flexibility of the system is decreased due to the required inflation lumen and dual layer construction needed to inflate the distal balloon. The combination of the large overall profile and the lack of distal flexibility makes tracking these devices in the neurovascular anatomy difficult. Accordingly, use of these devices is mostly limited to the proximal cerebral vasculature.

SUMMARY

To address these deficiencies in the existing art, a helical balloon assist device can include a tubular balloon formed at least partially into an independent helical shape in an uninflated state and an inflation tube in sealed communication with the balloon and extending from the helical balloon assist device in a proximal direction. The helical balloon assist device can also have an inner core member formed at least partially into an independent helical shape and supporting the helical shape of the tubular balloon. In examples, the inner core member may be formed of a resilient material.

Other examples have the inner core member secured to the balloon or secured to an interior portion of a balloon wall closest or farthest to a helical axis. The inner core member can be secured to a balloon wall by an adhesive, by welding, or by mechanical fastening. Other examples have the inner core member not secured to the balloon. The inner core member can be formed in a multiple helix shape with a second helix extending helically along a wall of the tubular balloon. Examples of the balloon include it being made of an elastic material or an inelastic material.

The helical balloon assist device can also have a positioner fabricated from a resilient material, and in certain examples, the positioner is the inflation tube. The positioner can be configured to position the helical balloon assist device in a radial direction.

The helical balloon assist device can be paired with a catheter system having a catheter and the helical balloon assist device, slidably engaging an outside of the catheter.

An exemplary method of using a helical balloon assist device can include the steps of deforming a distal turn of a balloon of the helical balloon assist device to create or expand a gap between turns of the balloon of the helical balloon assist device. Then inserting a catheter through the gap between the turns of the balloon, twisting the helical balloon assist device to fully mount the helical balloon assist device onto the catheter, and sliding the helical balloon assist device along the catheter, using an inflation tube or a positioner, to a treatment site in a patient's vasculature. The method can further include the steps of inflating the balloon of the helical balloon assist device using the inflation tube and then performing a clinical procedure. Afterwards, deflating the balloon of the helical balloon assist device using the inflation tube, and withdrawing the helical balloon assist device from the patient. In these examples, inflating the balloon of the helical balloon assist device causes at least a partial occlusion of a patient's blood vessel adjacent to the treatment site.

DETAILED DESCRIPTION

Figure 1:
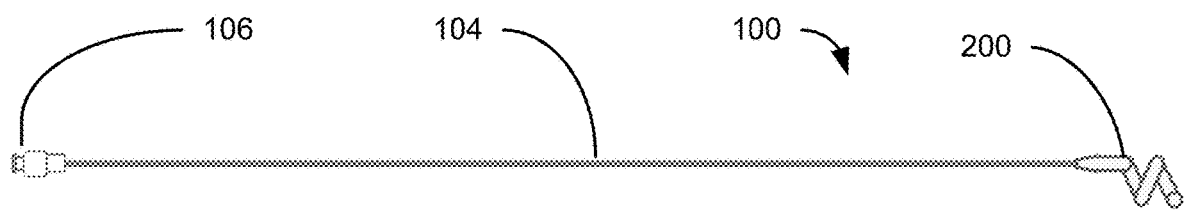
FIG. 1 is a diagram of the helical balloon assist device illustrating its basic components, in accordance with the present disclosure.
Figure 2:
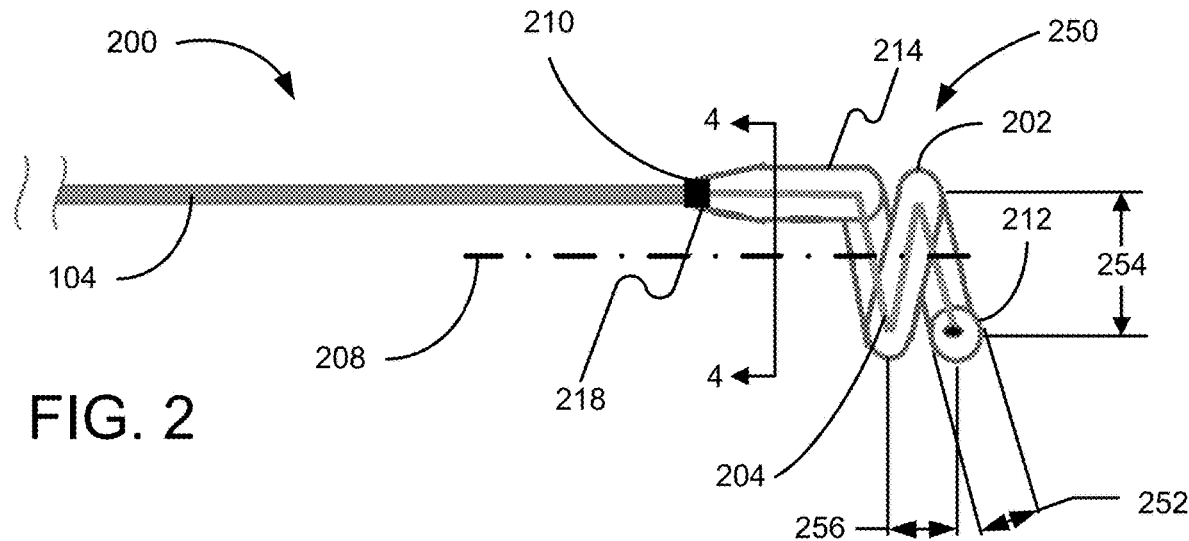
FIG. 2 is a diagram of the balloon assembly of the helical balloon assist device illustrating the balloon in the deflated state, in accordance with the present disclosure.
Figure 3:
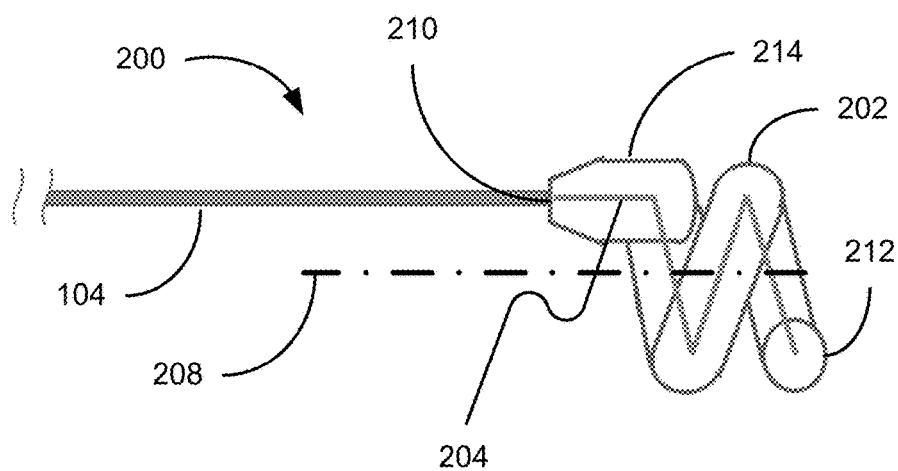
FIG. 3 is a diagram of the balloon assembly of the helical balloon assist device illustrating the balloon in the inflated state, in accordance with the present disclosure.

Referring now to the Figures, in which like reference numerals represent like parts, various examples of the helical balloon assist device and methods of using it will be disclosed in detail. FIG. 1 is a diagram of the helical balloon assist device illustrating is basic components. The helical balloon assist device 100 includes a balloon assembly 200, an inflation tube 104, and an inflation port 106. FIG. 2 is a closer view of the balloon assembly 200. The balloon assembly includes the balloon 202 supported by an inner core member 204. The balloon 202 can be formed from an elastic or semi-elastic material, like polyimide. The balloon 202 extends helically along and about an axis 208 from a proximal end 210 to a distal end 212. The inner core member 204 is a helical element supporting the balloon 202. In one example, the inner core member 204 may be a wire. Although a particular shape of the balloon 202 is illustrated, the disclosure is not limited to the shape shown.

The balloon 202 may have a straight section 214 at one or both ends which extends parallel to the axis 208. The straight section 214 may improve the robustness of the bond to the inflation tube 104, may improve the grip of the balloon 202 on a catheter 240, or may improve the ease of tracking the balloon 202 along the catheter 240. Alternatively, the balloon 202 may be purely helical. The helical portion 250 of the balloon 202 is described by a tube diameter 252, a nominal diameter 254 which defines the distance between the turns of the balloon 202 and the axis 208, and pitch 256 between turns of the balloon 202. The tube diameter 252 may be constant or variable. In some examples, the tube diameter 252 may taper toward the end 212 of the balloon 202. The pitch 256 may be constant or may be variable. In one example (not shown), the balloon 202 may have a "closed" end where a partial turn is non-helical, but instead has zero pitch and coils around the catheter following a plane perpendicular to the axis 208, similar to the "closed" end of a helical compression spring.

The balloon 202 is inflated using the inflation tube 104. Sterile water, saline, or another appropriate solution may be introduced to the inflation tube 104 at the inflation port 106. The inflation port 106 may be one of several types known in the industry. The inflation tube 104 has an open end 218 which terminates inside the balloon 202. The outer perimeter of the inflation tube 104 is bonded to balloon 202 at a location proximal to its open end 218. The bond provides a hermetic seal and a robust mechanical attachment to withstand forces during use of the helical balloon assist device 100.

The inflation tube 104 may be made from metal to facilitate pushability of the balloon 202 along the catheter 240, a polymeric material such as a polyimide for flexibility, or a combination of metal at the proximal end 210 and transitioning to the polymeric material as it extends toward the distal end 212. In some examples the inflation tube 104 may be used to position the helical balloon assist device 100 along the catheter 240 in the distal direction and to retract it in the proximal direction. In some examples, the inflation tube 104 may be attached to the inner core member 204. In other examples a separate positioner (not shown) may be attached to the balloon 202 and/or the inner core member 204 to advance the helical balloon assist device 100 along the catheter 240 in the distal direction and to retract it in the proximal direction, allowing the inflation tube 104 to be more flexible. The positioner may be made of a resilient material such as spring-temper stainless steel or, more preferably, Nitinol. In several examples the positioner may be attached by welding, for example by laser or ultrasonic means, by adhesive, by crimping, or by thermal staking, as may be appropriate depending on the materials of the positioner, the inner body 104, and/or the balloon 202.

A length L of the balloon assembly 200 may be relatively short in the axial direction. In one example, the balloon assembly 200 may be less than or equal to twice the outside diameter D of the catheter 240 (see, FIG. 6). In another example, the balloon assembly 200 may be less than or equal to the outside diameter D catheter 240. The short length L allows the balloon assembly 200 to track over tighter-radius bends of the catheter 240 which guides it.

Figure 4A:
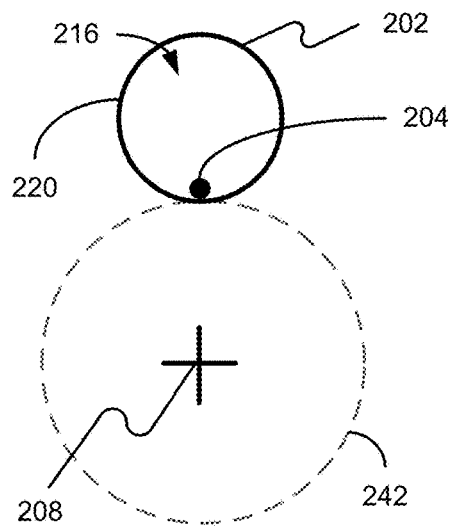
FIG. 4A is a cross-sectional diagram of the balloon assembly of the helical balloon assist device, illustrating one example of the inner core member positioned within the balloon close to the outside diameter of a catheter, in accordance with the present disclosure.
Figure 4B:
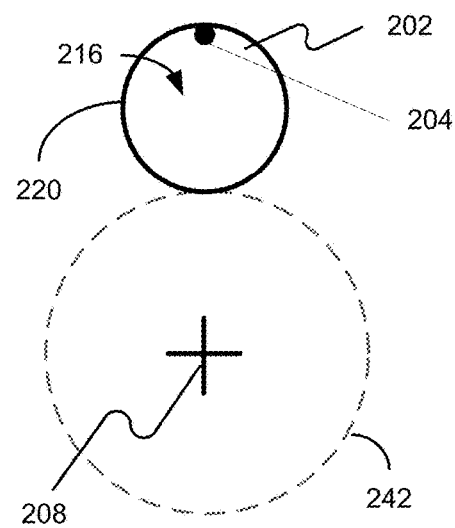
FIG. 4B is a cross-sectional diagram of the balloon assembly of the helical balloon assist device, illustrating one example of the inner core member positioned within the balloon far from the outside diameter of a catheter, in accordance with the present disclosure
Figure 4C:
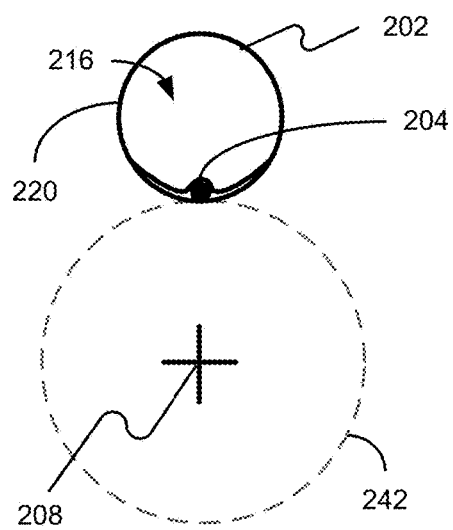
FIG. 4C is a cross-sectional diagram of the balloon assembly of the helical balloon assist device, illustrating one example of the inner core member positioned within the wall of the balloon, in accordance with the present disclosure

FIGS. 4A-4D illustrate examples of the inner core member 204. In one example, the inner core member 204 is made of a resilient material such as spring-temper stainless steel or, more preferably, a superelastic material such as Nitinol. The inner core member 204 has a helical shape which supports the balloon 202. The inner core member 204 may be secured to the balloon 202 or may be loose within the balloon 202. The inner core member 204 may be secured by an adhesive, by ultrasonic welding, by mechanical fasteners, by heat staking, or by other means known to those skilled in the art. If secured to the balloon 202, the inner core member 204 may be secured to the interior 216 of the balloon 202, the exterior of the balloon 202, or within a wall 220 of the balloon 202, as shown in FIG. 4C. The inner core member 204 may also be secured to the inflation tube 104 by an adhesive, by ultrasonic welding, by mechanical fasteners, by heat staking, or by other means known to those skilled in the art. In one example, the inner core member 204 may be formed into a helix following the wall 220 of the balloon 202 closest to the catheter 240, i.e., a helix having a nominal diameter similar to the outer diameter 242 of the catheter 240 as shown in FIG. 4A. In another example, the inner core member 204 may be formed into a helix following the wall 220 of the balloon 202 farthest to the catheter 240 as shown in FIG. 4B, i.e., a helix having a nominal diameter approximately equal to the outer diameter D (illustrated by a circumference 242) of the catheter 240 plus twice the tube diameter of the balloon 202.

Figure 4D:
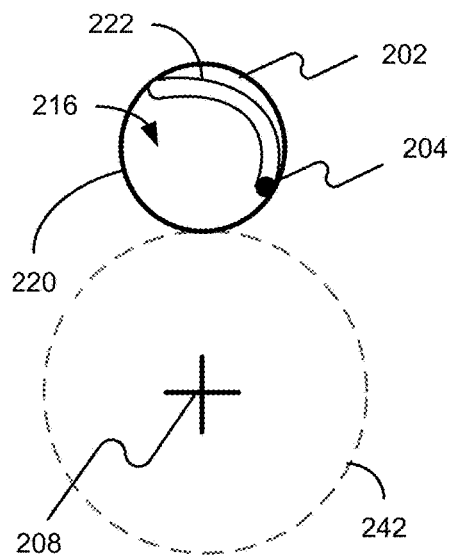
FIG. 4D is a cross-sectional diagram of the balloon assembly of the helical balloon assist device, illustrating one example of the inner core member positioned within the balloon, in a multiple-helix shape, in accordance with the present disclosure.

In another example, the inner core member 204 may be formed into a multiple helix 222 which helically follows the inside wall 220 of the helical shape of the balloon 202 as shown in FIG. 4D. The multiple helix 222 has a nominal diameter approximately equal to the tube diameter of the balloon and winds helically along an axis approximating a spline following the center of the balloon tube. Thus, the multiple helix 222 resembles a long coil spring wrapped around the catheter 240. The multiple helix 222 may be formed, for example, mechanically or by heat-treating the inner core member 204 on a form.

Figure 5:
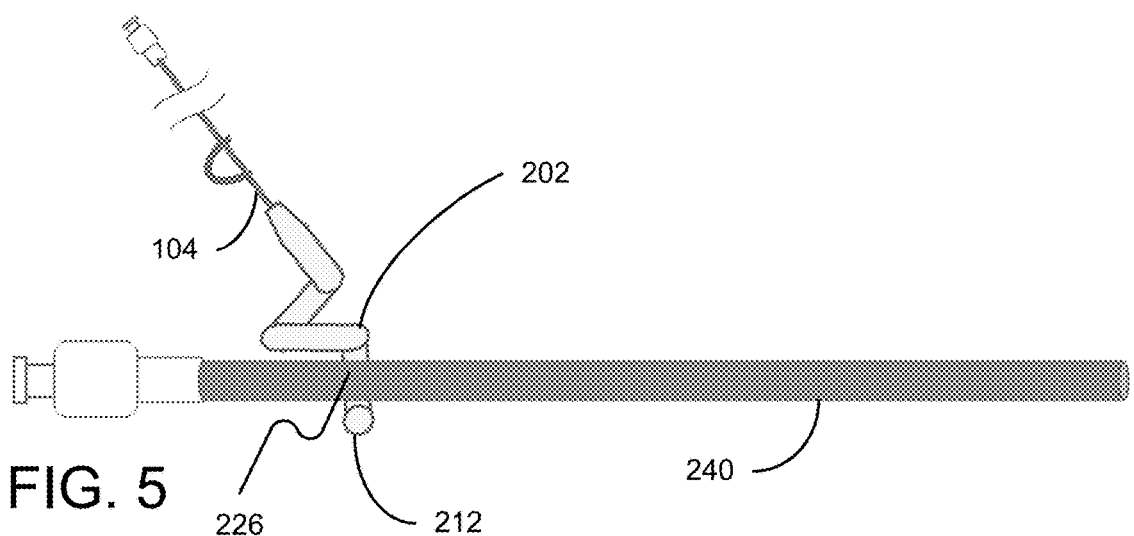
FIG. 5 is a diagram of mounting the helical balloon assist device on the proximal end of the catheter body, in accordance with the present disclosure.
Figure 6:
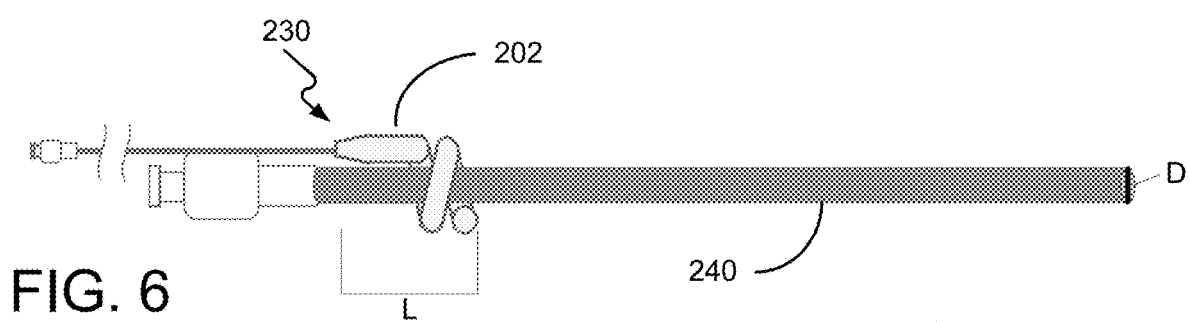
FIG. 6 is a diagram of mounting the helical balloon assist device fully mounted on the proximal end of the catheter body, in accordance with the present disclosure.
Figure 7:
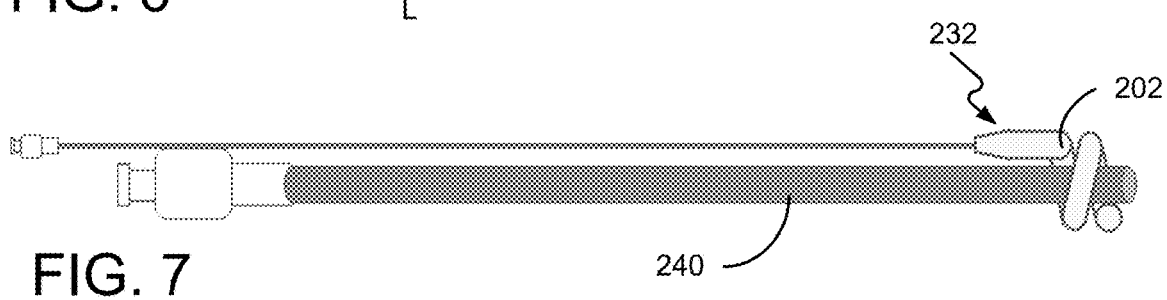
FIG. 7 is a diagram of the helical balloon assist device mounted on the catheter body and positioned at the distal end of the catheter, in accordance with the present disclosure.
Figure 8:
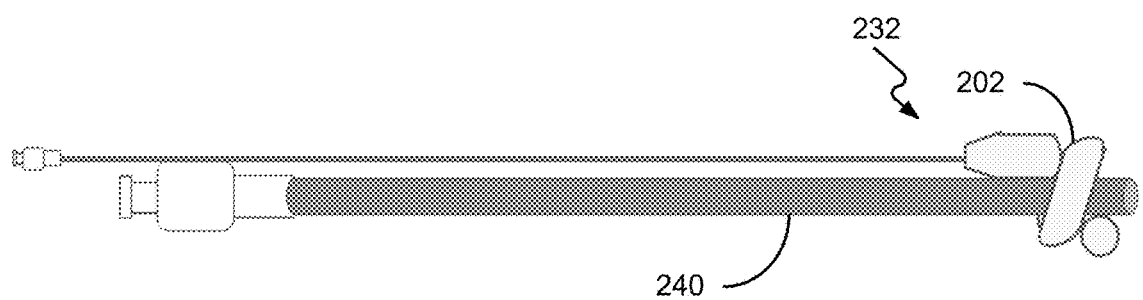
FIG. 8 is a diagram of the helical balloon assist device balloon inflated at the distal end of the catheter, in accordance with the present disclosure.

FIGS. 5-8 show the basic operation of the helical balloon assist device 100. FIG. 5 shows the balloon assist device being temporarily deformed and mounted on the catheter by twisting in a corkscrew fashion. The distal end 212 of the balloon 202 is deformed to create a gap 226 between the distal-most turn of the balloon 202 and the next-most distal turn. FIG. 6 shows the helical balloon assist device fully mounted on the catheter in a proximal position 230. The helical balloon assist device 100 is then slid along the catheter 240 using the inflation tube 104 or a separate positioner (not shown). FIG. 7 shows the helical balloon assist device 100 mounted on the catheter 240 in the distal position 232 after sliding along the catheter 240. The balloon 202 is then inflated using the inflation tube 104, as shown in FIG. 8.

Figure 9:
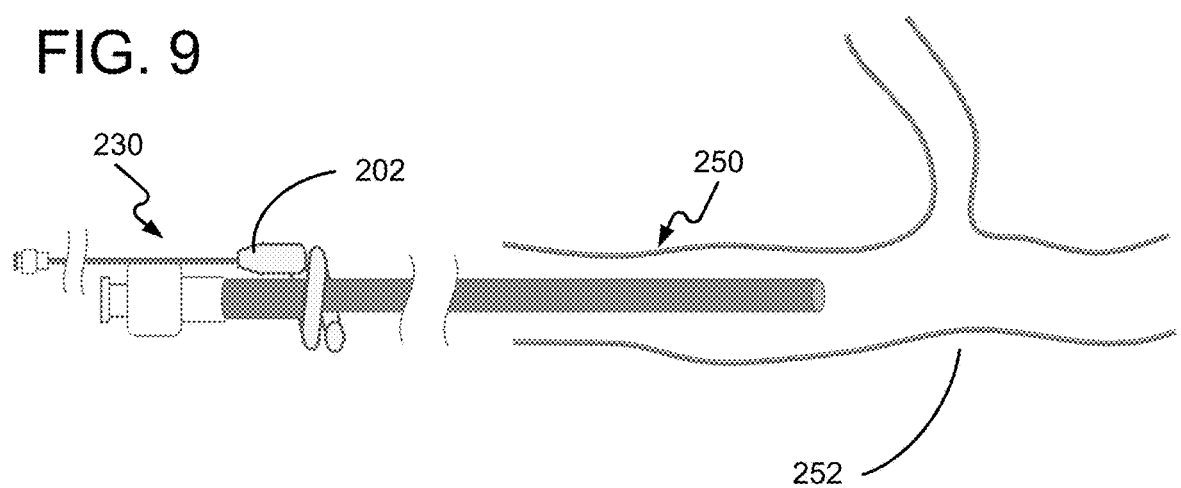
FIG. 9 is a diagram of a catheter positioned in a patient's vasculature with the helical balloon assist device mounted to the proximal end of the catheter body, in accordance with the present disclosure.
Figure 10:
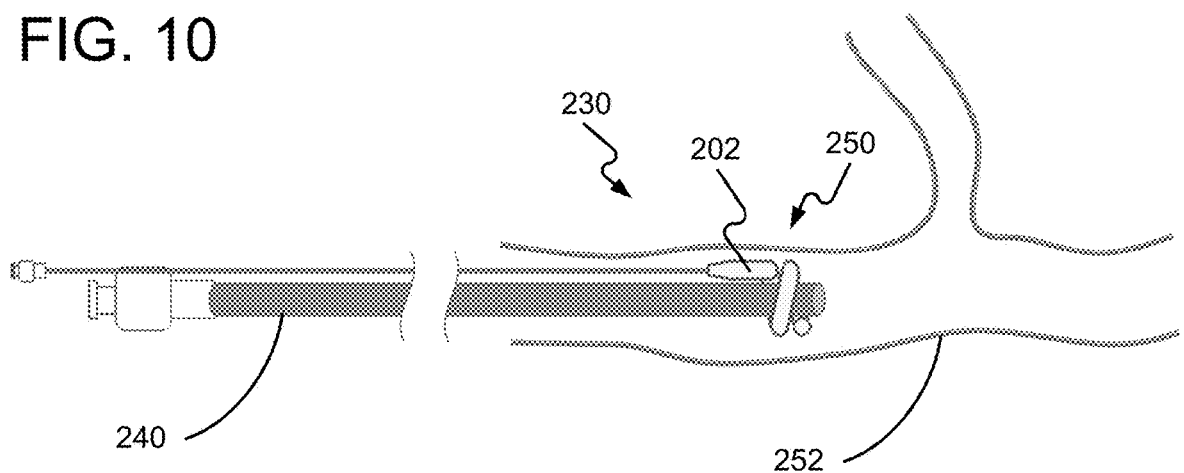
FIG. 10 is a diagram of a catheter positioned in a patient's vasculature with the helical balloon assist device positioned on the distal end of the catheter body at the treatment site, in accordance with the present disclosure.
Figure 11:
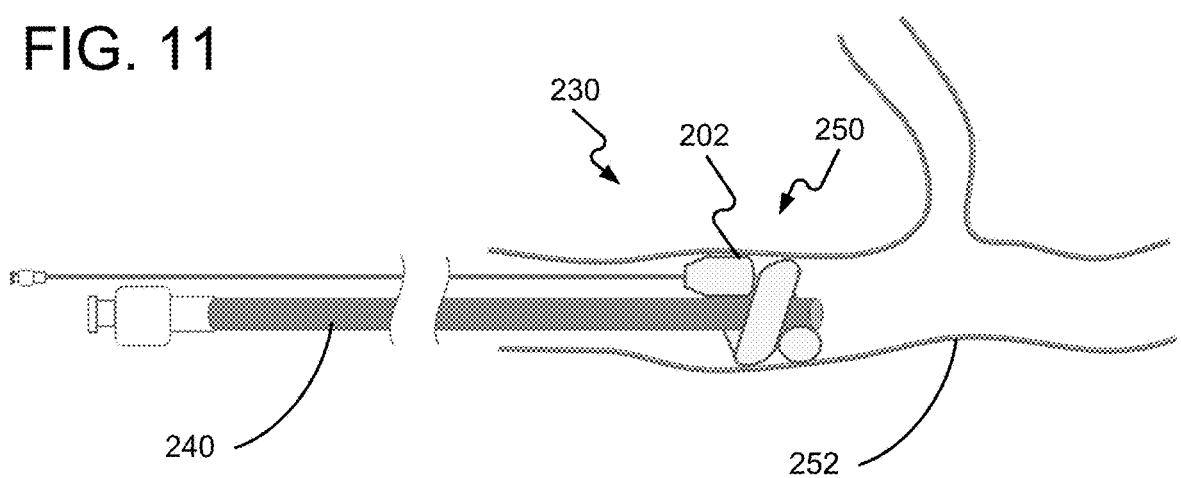
FIG. 11 is a diagram of a catheter positioned in a patient's vasculature with the balloon inflated at the treatment site, occluding a blood vessel, in accordance with the present disclosure.

FIGS. 9-11 show the basic operation of the helical balloon assist device 100 during a medical procedure. FIG. 9 shows the helical balloon assist device 100 fully mounted in the proximal position 230 on a catheter 240 which a clinician may have already positioned at a treatment site 250 within a patient's vasculature 252. The helical balloon assist device 100 is then slid along the catheter 240 using the inflation tube 104 or a separate positioner (not shown) to treatment site 250. FIG. 10 shows the helical balloon assist device 100 mounted on the catheter 240 in the distal position 232 at the treatment site 250. The balloon 202 is then inflated using the inflation tube 104 to occlude part of the patient's vasculature 252, as shown in FIG. 11. In some examples, helical balloon assist device 100 may be used during a clinical procedure to occlude blood flow, to occlude or capture tissue, plaques, or debris liberated by the procedure, or to hold the catheter 240 in position in the blood vessel.

Figure 12:
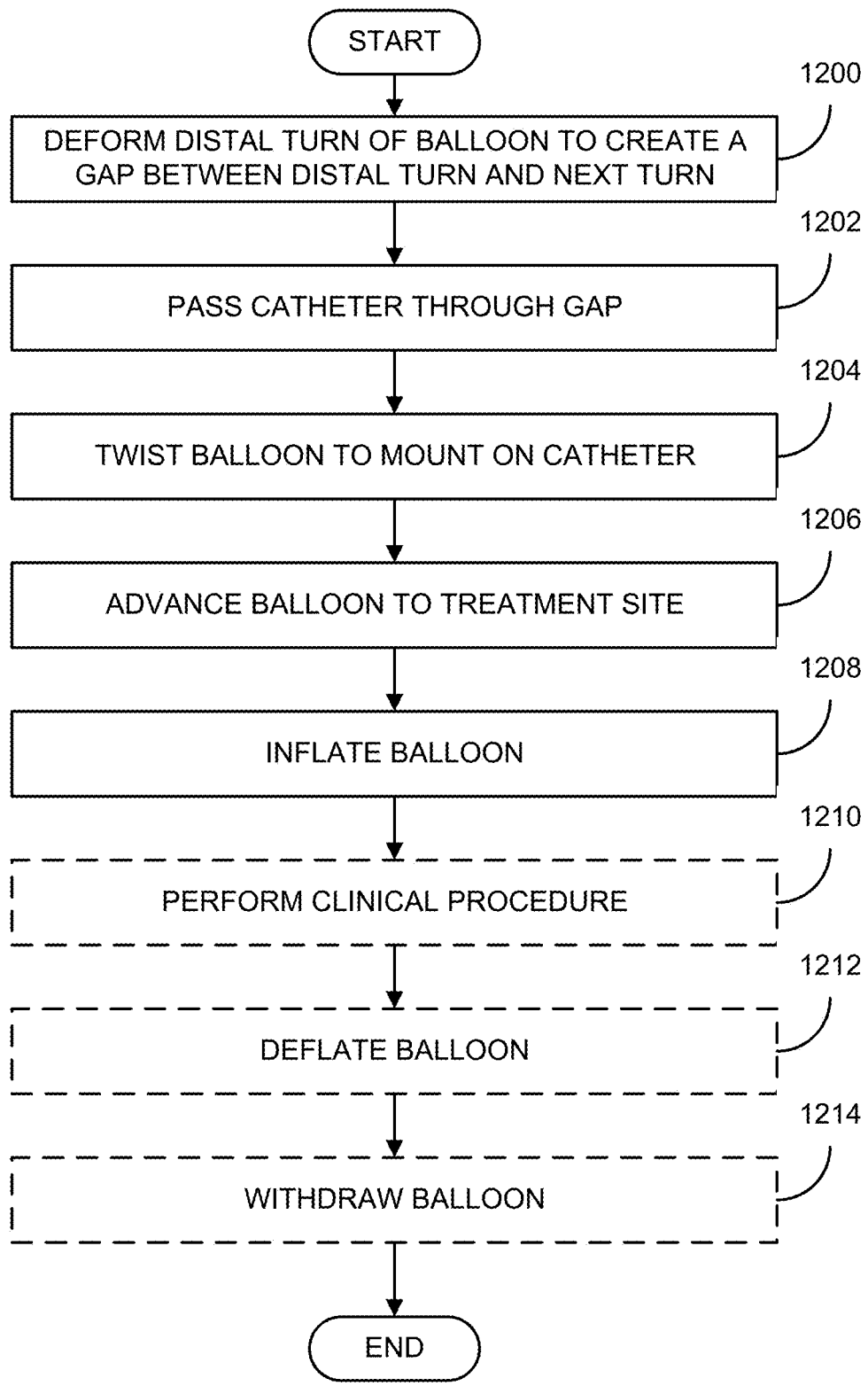
FIG. 12 is a flow chart illustrating one example of a method for using the helical balloon assist device, in accordance with the present disclosure.

FIG. 12 is flow chart showing the steps for using the helical balloon assist device 100. At 1200 the distal end of the balloon is deformed to create or expand a gap 226 between turns of the helix. At 1202 the catheter 240 is inserted through the gap 226 between the turns of the balloon 202. At 1204 the helical balloon assist device 100 is twisted fully onto the catheter 240 in a corkscrew fashion. At 1206 the inflation tube 104 or a positioner is used to slide the helical balloon assist device 100 along the catheter 240 to a treatment site 250 in a patient's vasculature 252. In some examples the positioner may be the inflation tube 104. At 1208 the helical balloon assist device 100 is inflated at the treatment site 250 using the inflation tube 104. The remaining steps are optional based on the clinical procedure. At 1210 a procedure is performed while the inflated helical balloon assist device 100 occludes a blood vessel at the treatment site 250. At 1212 the helical balloon assist device 100 is deflated. At 1214 the deflated helical balloon assist device 100 is withdrawn.

To facilitate an understanding of the principals and features of the disclosed technology, illustrative examples are explained above. The components described hereinafter as making up various elements of the disclosed technology are intended to be illustrative and not restrictive. Many suitable components that would perform the same or similar functions as components described herein are intended to be embraced within the scope of the disclosed devices and methods. Such other components not described herein may include, but are not limited to, for example, components developed after development of the disclosed technology.

Although the examples describe mounting the helical balloon assist device on a catheter, it may similarly be employed with a guidewire, lumen, or any similarly elongated vascular surgical tool.

It must also be noted that, as used in the specification and the appended claims, the singular forms "a," "an" and "the" include plural referents unless the context clearly dictates otherwise. By "comprising" or "containing" or "including" is meant that at least the named component or method step is present in the article or method, but does not exclude the presence of other components or method steps, even if the other such components or method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art.

Certain examples of this technology are described above with reference to flow diagrams. Some blocks of the block diagrams and flow diagrams may not necessarily need to be performed in the order presented, or may not necessarily need to be performed at all, according to some examples of the disclosure.

While certain examples of this disclosure have been described in connection with what is presently considered to be the most practical and various examples, it is to be understood that this disclosure is not to be limited to the disclosed examples, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain examples of the technology and also to enable any person skilled in the art to practice certain examples of this technology, including making and using any apparatuses or systems and performing any incorporated methods. The patentable scope of certain examples of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method comprising:
   deforming a helical portion of a balloon thereby creating or expanding a gap between two turns of the balloon;
   inserting a catheter through the gap between the two turns of the balloon such that at least a portion of the two turns of the balloon contacts an outside of a body of the catheter;
   twisting the balloon to fully mount the helical portion onto the outside of the body of the catheter; and
   sliding a distalmost end of the helical portion along the outside of the body of the catheter by pushing an inflation tube extending from the balloon in a proximal direction along the outside of the body of the catheter.

2. The method of claim 1, wherein sliding the helical portion along the outside of the catheter includes sliding the inflation tube along the outside of the catheter.

3. The method of claim 1 further comprising inflating the balloon using the inflation tube.

4. The method of claim 3, wherein inflating the balloon causes at least a partial occlusion of a blood vessel adjacent to a treatment site.

5. The method of claim 3, wherein inflating the balloon entirely inhibits blood flow through a portion of a blood vessel in which the helical portion of the balloon is positioned.

6. The method of claim 5 further comprising deflating the balloon using the inflation tube.

7. The method of claim 6 further comprising withdrawing the balloon from a patient.

8. The method of claim 7, wherein withdrawing the balloon from the patient comprises pulling the inflation tube in a proximal direction.

9. A method of occluding a blood vessel in a patient, the method comprising:
   sliding a distalmost end of a tubular balloon along an outside of a catheter by pushing an inflation tube to a treatment site in vasculature of the patient while the distalmost end is formed in a helical shape wrapped about a circumference of the outside of a body of the catheter and the inflation tube extends in a proximal direction from the distalmost end; and
   inflating the tubular balloon using the inflation tube.

10. The method of claim 9, wherein sliding the distalmost end of the tubular balloon along the outside of the catheter includes sliding the inflation tube along the outside of the catheter.

11. The method of claim 9, wherein inflating the tubular balloon using the inflation tube causes at least a partial occlusion of the blood vessel adjacent to the treatment site.

12. The method of claim 11, wherein inflating the tubular balloon entirely inhibits blood flow through the vasculature at the treatment site.

13. The method of claim 12 further comprising deflating the tubular balloon using the inflation tube.

14. The method of claim 13 further comprising withdrawing the tubular balloon from the patient.

15. The method of claim 14, wherein withdrawing the tubular balloon from the patient comprises pulling the inflation tube in a proximal direction.

16. The method of claim 9 further comprising supporting the helical shape of the distal end by an inner core member formed at least partially into a second helical shape.

17. A method of occluding a blood vessel, the method comprising:
   positioning a catheter across an occlusion site within the blood vessel;
   sliding a helical portion of a balloon distally over an outside of a catheter to the occlusion site while the helical portion is wrapped about the outside of the catheter; and
   inflating the balloon, thereby inhibiting blood flow through the blood vessel at the occlusion site.

18. The method of claim 17 further comprising:
   deforming the helical portion of the balloon thereby creating or expanding a gap between two turns of the balloon; and
   inserting the catheter through the gap between the two turns of the balloon such that at least a portion of the two turns of the balloon contacts the outside of the catheter.

19. The method of claim 17 further comprising pushing an inflation tube extending proximally from the balloon to thereby slide the helical portion of the balloon distally over the outside of the catheter to the occlusion site.

20. The method of claim 19 further comprising:
   withdrawing the inflation tube and the balloon from the blood vessel; and
   separating the inflation tube and balloon from the catheter.

* * * * *